(12) United States Patent
Payne et al.

(10) Patent No.: US 8,735,843 B2
(45) Date of Patent: May 27, 2014

(54) COMPOUNDS FOR NEUTRON RADIATION DETECTORS AND SYSTEMS THEREOF

(71) Applicant: Lawrence Livermore National Security, LLC, Livermore, CA (US)

(72) Inventors: Stephen A. Payne, Castro Valley, CA (US); Wolfgang Stoeffl, Livermore, CA (US); Natalia P. Zaitseva, Livermore, CA (US); Nerine J. Cherepy, Oakland, CA (US); M. Leslie Carman, San Ramon, CA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 0 days.

(21) Appl. No.: 13/736,898

(22) Filed: Jan. 8, 2013

(65) Prior Publication Data

US 2013/0181135 A1    Jul. 18, 2013

Related U.S. Application Data

(63) Continuation of application No. 12/418,450, filed on Apr. 3, 2009.

(51) Int. Cl.
*G01T 3/00* (2006.01)

(52) U.S. Cl.
USPC .................................................. 250/390.01

(58) Field of Classification Search
USPC .................. 250/390.01–390.12, 269.1–269.8
See application file for complete search history.

(56) References Cited

U.S. PATENT DOCUMENTS

| | | | |
|---|---|---|---|
| 3,116,417 A | 12/1963 | Orr et al. | |
| 3,750,046 A | 7/1973 | Buehler et al. | |
| 4,482,808 A | 11/1984 | Tominaga et al. | |
| 4,692,266 A | 9/1987 | Costa et al. | |
| 5,726,453 A | 3/1998 | Lott et al. | |
| 5,872,363 A | 2/1999 | Bingham et al. | |
| 5,940,460 A | 8/1999 | Seidel et al. | |
| 6,544,442 B1 | 4/2003 | Bell et al. | |
| 7,164,138 B2 | 1/2007 | McGregor et al. | |
| 8,207,507 B2 | 6/2012 | Zaitseva et al. | |
| 8,461,546 B2 | 6/2013 | Payne et al. | |
| 2006/0086311 A1 | 4/2006 | Zagumennyi et al. | |
| 2007/0175383 A1* | 8/2007 | Fukuda et al. | 117/35 |
| 2008/0017804 A1 | 1/2008 | Krishnamoorthy et al. | |
| 2010/0256923 A1 | 10/2010 | Payne et al. | |
| 2011/0266643 A1 | 11/2011 | Engelmann et al. | |
| 2011/0284755 A1 | 11/2011 | Stradins et al. | |
| 2012/0326042 A1 | 12/2012 | Zaitseva et al. | |

OTHER PUBLICATIONS

On line product catalog, down-loaded on Jun. 18, 2013, "Tri-Carb 2910 TR Liquid Scintillation Analyzer", PerkinElmer.*

(Continued)

*Primary Examiner* — Kiho Kim
(74) *Attorney, Agent, or Firm* — Dominic M. Kotab

(57) ABSTRACT

A material according to one embodiment exhibits an optical response signature for neutrons that is different than an optical response signature for gamma rays, said material exhibiting performance comparable to or superior to stilbene in terms of distinguishing neutrons from gamma rays, wherein the material is not stilbene, the material comprising a molecule selected from a group consisting of: two or more benzene rings, one or more benzene rings with a carboxylic acid group, one or more benzene rings with at least one double bound adjacent to said benzene ring, and one or more benzene rings for which at least one atom in the benzene ring is not carbon.

18 Claims, 11 Drawing Sheets

(56) References Cited

OTHER PUBLICATIONS

Non-Final Office Action from U.S. Appl. No. 12/418,450 dated Jul. 13, 2011.
Non-Final Office Action from U.S. Appl. No. 12/418,450 dated Nov. 15, 2011.
Final Office Action from U.S. Appl. No. 12/418,450 dated Feb. 24, 2012.
Non-Final Office Action from U.S. Appl. No. 12/418,450 dated Jun. 14, 2012.
Notice of Allowance and Fee(s) Due from U.S. Appl. No. 12/418,450 dated Oct. 22, 2012.
Wang et al., "Morphological instability of crystals grown from thin aqueous solution films with a free surface," 1995 Taylor & Francis Ltd., Philosophical Magazine A, 1995, vol. 71, No. 2, pp. 409-419.
Zhao et al., "Characteristics of large-sized Ce:YAG scintillation crystal grown by temperature gradient technique," 2003 Elsevier Science B.V., Journal of Crystal Growth, vol. 253, 2003, pp. 290-296.
Bryan et al., "Fast Neutron—Gamma Pulse Shape Discrimination of Liquid Scintillation Signals for Time Correlated Measurements," Nuclear Science Symposium Conference Record, 2003 IEEE, Oct. 19-25, 2003, vol. 2, pp. 1192-1195.
Jhingan et al, "Simple Ways of n-y Discrimination Using Charge Comparison Technique," ScienceDirect, Nuclear Instruments and Methods in Physics Research A 858 (2008) 165-171.
Soderstrom, P et al, "Digital Pulse-Shape Discrimination of Fast Neutrons and y Rays," ScienceDirect, Nuclear Instruments and Methods in Physics Research A 594 (2008) 79-89.
Lawrence Livermore National Laboratory, "Laboratory Directed Research and Development, FY2007 Annual Report."
Greenwood et al., "Li-Salicylate Neutron Detectors with Pulse Shape Discrimination," Nuclear Instruments and Methods 165 (1979) 129-131.
Non-Final Office Action from U.S. Appl. No. 12/418,434 dated May 20, 2011.
Non-Final Office Action from U.S. Appl. No. 12/418,434 dated Nov. 22, 2011.
Notice of Allowance and Fee(s) Due from U.S. Appl. No. 12/418,434 dated Feb. 23, 2012.
Sangster et al., "Study of Organic Scintillators," The Journal of Chemical Physics, vol. 24, No. 4, Apr. 1956, pp. 670-715.
Greenwood, L R. et al., "Li-Salicylate Neutron Detectors With Pulse Shape Discrimination," North-Holland Publishing Co., Nuclear Instruments and Methods, vol. 165, Received Jun. 5, 1979, pp. 129-131.
Brooks, F. D., "Development of Organic Scintillators," North-Holland Publishing Co., Nuclear Instruments and Methods, vol. 162, 1979, pp. 477-505.
Vijayan et al., "Growth, optical, thermal and mechanical studies of methyl 4-hydroxybenzoate single crystals," 2003 Elsevier B.V., Journal of Crystal Growth, vol. 256, 2003, pp. 174-182.
Peurrung, A. J., "Recent developments in neutron detection," 2000 Elsevier Science B.V., Nuclear Instruments and Methods in Physics Research A, vol. 443, 2002, pp. 400-415.
Mandshukov, et al., "Properties of a New Class of Organic Scintillators: Derivatives of Salicyclic Acid," 1982 Plenum Publishing Corporation, University of Sofia, Bulgaria, translated from Pribory i Tekhnika Eksperimenta, No. 3, pp. 45-50, May-Jun. 1981, pp. 605-611.
Varfolomeeva, et al., "Polarization Diagrams for the Fluorescence of Single Crystals of Salicyclic Acid and Salicylates," Soviet Physics—Crystallography, vol. 13, No. 2, Sep.-Oct. 1968, pp. 209-211.
Bryan et al., "Fast Neutron—Gamma Pulse Shape Discrimination of Liquid Scintillation Signals for Time Correlated Measurements," 2003 IEEE Nuclear Science Symposium Conference Record, Oct. 19-25, 2003, pp. 1-5.
Jhingan, et al., "Simple ways of n-y discrimination using charge comparison technique," 2007 Elsevier, B.V., Nuclear Intruments and Methods in Physics Research A., vol. 585, 2008, pp. 165-171.
Soderstrom et al., "Digital pulse-shape discrimination of fast neutrons and y rays," 2008 Elsevier B.V., Nuclear Instruments and Methods in Physics Research A., vol. 594, 2008, pp. 79-89.
"Laboratory Directed Research and Development, FY2007 Annual Report," Lawrence Livermore National Laboratory, 2007, pp. 1-262.
Soderstrom, P., "Pulse Shape Discrimination Between Neutrons and Gamma Rays with Digital Electronics," Nuclear Structure Group, Department of Nuclear and Particle Physics, Uppsala University, 2008, pp. 1-27.
Sellin et al., "Digital Pulse Shape Discrimination Applied to Capture-Gated Neutron Detectors," Department of Physics, University of Surrey, Guildford, UK, 2008, pp. 1-18.
Anutgan et al., "Effect of heat treatment on the stress and structure evolution of plasma deposited boron nitride thin films," Surface & Coatings Technology, vol. 202, 2008, pp. 3058-3066.
Dusane, R. O., "Opportunities for new materials synthesis by hot wire chemical vapor process," Thin Solid Films, vol. 519, 2011, pp. 4555-4560.
Lattemann et al., "New approach in depositing thick, layered cubic boron nitride coatings by oxygen addition—structural and compositional analysis," Thin Solid Films, vol. 515, 2006, pp. 1058-1062.
Bello et al., "Deposition of thick cubic boron nitride films: The route to practical applications," Diamond & Related Materials, vol. 14, 2005, pp. 1154-1162.
He et al., "Improvement of adhesion of cubic boron nitride filsm: effect of interlayer and deposition parameters," Materials Science Forum, vols. 475-479, 2005, pp. 3637-3638.
Shultis et al., "Efficiencies of Coated and Perforated Semiconductor Neutron Detectors," 2004 IEEE, pp. 4569-4574.
McGregor et al., "New Surface Morphology for Low Stress Thin-Film-Coated Thermal Neutron Detectors," 2002 IEEE, IEEE Transactions on Nuclear Science, vol. 49, No. 4, Aug. 2002, pp. 1999-2004.
Matsumoto et al., "The introducing of fluorine into the deposition of BN: a successful method to obtain high-quality, thick cBN films with low residual stress," Diamond and Related Materials, vol. 10, 2001, pp. 1868-1874.
Karim et al., "Effect of deposition parameters on the formation of cubic BN films deposited by plasma-assisted chemical vapour deposition from non-toxic material," Surface and Coatings Technology, vol. 54-55, 1992, pp. 355-359.
Notice of Allowance and Fee(s) Due from U.S. Appl. No. 13/439,780 dated Jul. 31, 2013.
Zaitseva et al., "Neutron detection with single crystal organic scintillators," SPIE Hard X-Ray, Gamma-Ray, and Neutron Detector Physics, Lawrence Livermore National Laboratory, Jul. 20, 2009, pp. 1-10.

* cited by examiner

COMPOUNDS FOR NEUTRON RADIATION DETECTORS AND SYSTEMS THEREOF

RELATED APPLICATIONS

This application is a continuation of U.S. patent application Ser. No. 12/418,450, filed Apr. 3, 2009, which is herein incorporated by reference.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to radiation detection, and more particularly to compounds for neutron radiation detectors and related methods.

BACKGROUND

Radioactive materials are often detected and identified by measuring gamma-rays and/or neutrons emitted from the materials. The energy of gamma-rays is specific to that particular material and acts as a "finger print" to identify the material. Similarly, neutron energy is particular to the material, and may be used to identify the material. Of very high value are detectors capable of identifying the distinctive time-correlated signatures corresponding to neutrons and gammas emitted by fissioning material from within a background of uncorrelated natural radiation. A detector capable of distinguishing neutrons from gammas, as well as offering a fast response time typically has better capability for detecting the distinctive time-correlated events indicative of the presence of fissioning nuclei.

The ability to detect gamma rays and/or neutrons is a vital tool for many areas of research. Gamma-ray/neutron detectors allow scientists to study celestial phenomena and diagnose medical diseases, and they have been used to determine the yield in an underground nuclear test. Today, these detectors are important tools for homeland security, helping the nation confront new security challenges. The nuclear nonproliferation mission requires detectors capable of identifying diversion of or smuggling of nuclear materials. Government agencies need detectors for scenarios in which a terrorist might use radioactive materials to fashion a destructive device targeted against civilians, structures, or national events. To better detect and prevent nuclear incidents, the Department of Energy (DOE) and the Department of Homeland Security (DHS) are funding projects to develop a suite of detection systems that can search for radioactive sources in different environments.

One particularly useful type of radiation detection, pulse shape discrimination (PSD), which is exhibited by some organic scintillators, involves subtle physical phenomena which give rise to the delayed luminescence characteristic of neutrons, providing a means of distinguishing neutrons from the preponderance of prompt luminescence arising from background gamma interactions. The mechanism by which this occurs begins with intersystem crossing (ISC), where the excited singlet state (S1) nonradiatively relaxes to the excited triplet (T), as shown in FIG. 1. In FIG. 1, the basic physical processes leading to the delayed fluorescence characteristic of neutron excitation of organics with phenyl groups is shown.

Since the triplet is known to be mobile in some compounds, the energy migrates until two triplets collide and experience an Auger upconversion process, shown as Equation 1:

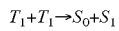                                                           Equation 1

In Equation 1, T1 is a triplet, $S_0$ is the ground state, and $S_1$ is a first excited state. Finally, the delayed singlet emission occurs with a decay rate characteristic of the migration rate and concentration of the triplet population, which is represented as Equation 2:

                                                           Equation 2

In Equation 2, hv is fluorescence, while $S_0$ is the ground state and $S_1$ is a first excited state. The enhanced level of delayed emission for neutrons arises from the short range of the energetic protons produced from neutron collisions (thereby yielding a high concentration of triplets), compared to the longer range of the electrons from the gamma interactions. The resulting higher concentration of triplets from neutrons, compared to gamma interactions, leads to the functionality of PSD. The observation of PSD is believed to be in part related to the benzene ring structure, allowing for the migration of triplet energy.

It is generally accepted in the prior art that stilbene offers good PSD. However, stilbene, generally grown from melt, is difficult to obtain. Therefore, a number of other organic molecules have been examined. Unfortunately, most research in this area has concluded that other known liquid and solid materials, including many compounds having benzene rings, do not possess PSD properties comparable to single-crystal stilbene.

Accordingly, it would be beneficial to provide organic materials which may be comparable to or better than stilbene in relation to PSD properties for neutron radiation detection.

SUMMARY

A material according to one embodiment exhibits an optical response signature for neutrons that is different than an optical response signature for gamma rays, said material exhibiting performance comparable to or superior to stilbene in terms of distinguishing neutrons from gamma rays, wherein the material is not stilbene, the material comprising a molecule selected from a group consisting of:
- two or more benzene rings,
- one or more benzene rings with a carboxylic acid group,
- one or more benzene rings with at least one double bound adjacent to said benzene ring, and
- one or more benzene rings for which at least one atom in the benzene ring is not carbon.

A system may include the foregoing material, and a photodetector for detecting the response of the material to neutron and gamma ray irradiation.

A method according to one embodiment includes growing an organic crystal from solution, the organic crystal exhibiting an optical response signature for neutrons that is different than an optical response signature for gamma rays, said material exhibiting performance comparable to or superior to stilbene in terms of distinguishing neutrons from gamma rays, wherein the material is not stilbene.

In one approach, the crystal comprises a material selected from a group consisting of:
- 1-1-4-4-tetraphenyl-1-3-butadiene;
- 2-fluorobiphenyl-4-carboxylic acid;
- 4-biphenylcarboxylic acid;
- 9-10-diphenylanthracene;
- 9-phenylanthracene;

1-3-5-triphenylbenzene;
m-terphenyl;
bis-MSB;
diphenylacetylene;
2-5-diphenyoxazole;
4-benzylbiphenyl;
biphenyl;
4-methoxybiphenyl;
n-phenylanthranilic acid; and
1-4-diphenyl-1-3-butadiene.

In another approach, the crystal comprising a molecule selected from a group consisting of:
two or more benzene rings,
one or more benzene rings with a carboxylic acid group,
one or more benzene rings with at least one double bound adjacent to said benzene ring, and
one or more benzene rings for which at least one atom in the benzene ring is not carbon.

The crystal may have a length of greater than 1 mm in one dimension, in some embodiments greater than 5 mm in one dimension, and in yet other embodiments greater than 25 mm in one dimension.

The solution may include a solvent and a solute, the solvent comprising more than 30% of said solution, and said solution being held at a temperature that is less than that of the melting point of said solute during the growing.

Other aspects and embodiments of the present invention will become apparent from the following detailed description, which, when taken in conjunction with the drawings, illustrate by way of example the principles of the invention.

DETAILED DESCRIPTION

Figure 1:
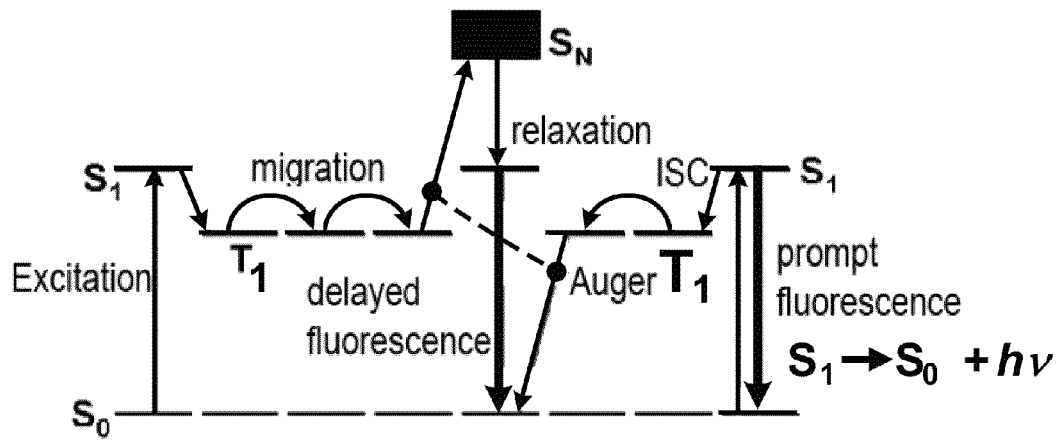
FIG. 1 shows a mechanism for delayed photoluminescence according to the prior art.
Figure 1:
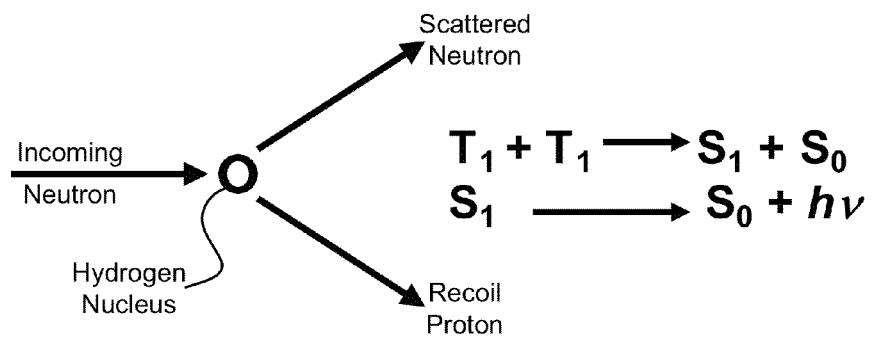

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

In one general embodiment, a substantially pure crystal exhibiting an optical response signature for neutrons that is different than an optical response signature for gamma rays comprises a material selected from a group consisting of: 1-1-4-4-tetraphenyl-1-3-butadiene; 2-fluorobiphenyl-4-carboxylic acid; 4-biphenylcarboxylic acid; 9-10-diphenylanthracene; 9-phenylanthracene; 1-3-5-triphenylbenzene; m-terphenyl; bis-MSB; diphenylacetylene; 2-5-diphenyoxazole; 4-benzylbiphenyl; biphenyl; 4-methoxybiphenyl; n-phenylanthranilic acid; and 1-4-diphenyl-1-3-butadiene. By "substantially pure crystal," what is meant is that the crystal comprises greater than about 95 mol %, more preferably more than about 98 mol %, even more preferably more than about 99 mol % of the primary material.

In another general embodiment, a material exhibits an optical response signature for neutrons that is different than an optical response signature for gamma rays, wherein the material exhibits performance comparable to or superior to stilbene in terms of distinguishing neutrons from gamma rays, wherein the material is not stilbene.

Advanced digital techniques enable PSD properties of materials to be more effectively determined, thereby allowing a greater understanding of the ability of a material to act as a good scintillator material. Certain types of scintillators are used for PSD, such as liquids, plastics, and single crystal scintillators. In the realm of single crystal scintillators, stilbene is the probably the most thoroughly investigated and used. It has high PSD performance, high cost, and low availability, sometimes requiring several months of waiting time in order to receive the size and/or weight for specific applications.

Organic crystals which are capable of good PSD are desired for use as scintillators. Unfortunately, there are no general guidelines or correlation which could lead one of ordinary skill in the relevant art to predict which crystals would make good scintillators. Accordingly, each time an organic crystal having good PSD properties is found, the result is surprising and unexpected.

It has been surprisingly found that certain materials exhibit pulse shape discrimination (PSD) properties close to and/or better than stilbene, which may be used as a reference for which materials may perform well in gamma radiation detection applications. Among such materials, some of the most promising include 1-1-4-4-tetraphenyl-1-3-butadiene, 2-fluorobiphenyl-4-carboxylic acid, 1-3-5-triphenylbenzene, and 9-10-diphenylanthracene, which, in addition to having desirable properties, have also been found to be able to be grown from solution.

Other materials which have been surprisingly found to exhibit PSD properties close to and/or better than stilbene include, 4-biphenyl carboxylic acid, m-terphenyl, bis-MSB, diphenylacetylene, 2,5-diphenyoxazole, 4-benzylbiphenyl, biphenyl, 4-methoxybiphenyl, n-phenylanthranilic acid, and 1,4-diphenyl-1,3-butadiene. Many of these materials had not been grown as crystals before, which is critical to effective testing for desirable scintillator properties, such as PSD. In addition, the signature may be different for each type of material and/or neutron source, but a given material will tend to show similar response for a given neutron type and/or source.

Because stilbene is used widely as a scintillator, the PSD properties of stilbene were used as a reference for selection of other efficient PSD materials.

Figure 2A:
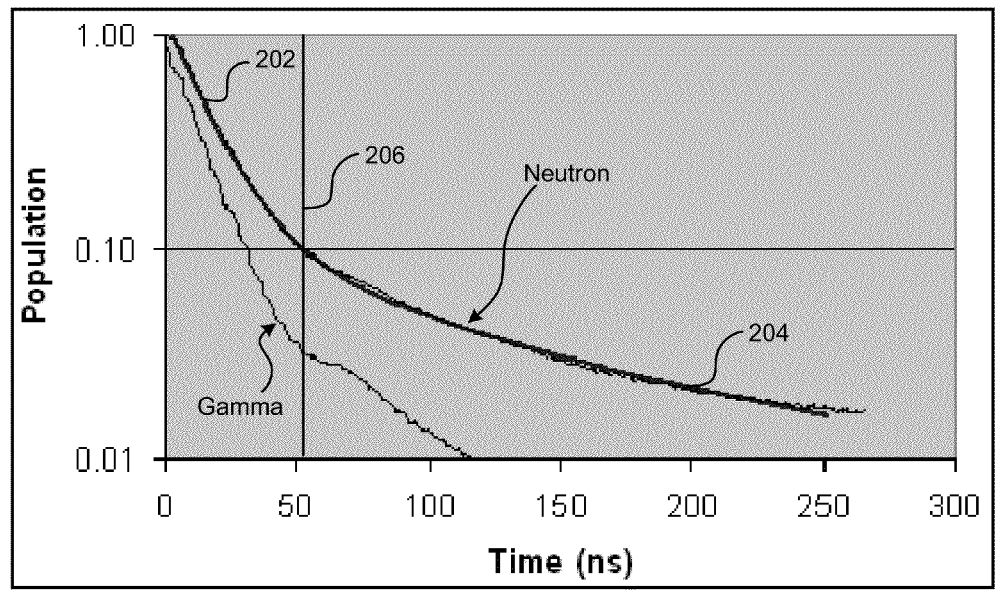
FIG. 2A shows a plot of Population versus Time for stilbene according to one embodiment.

FIG. 2A shows a plot of logarithmic population versus linear time (ns) for stilbene. Population is the singlet excited state population, which is proportionally to the output of light from a test crystal under examination, in this case a stilbene crystal, after the crystal it is excited by high energy radiation. As can be seen from the plot, some light is produced by the crystal almost immediately, referred to as prompt luminescence, and other light is produced from the crystal over a period of time, referred to as delayed luminescence. Generally, the plot for each type of radiation will have a steep component 202 and a tail component 204, where the differentiation point 206 between the two is defined in the region where the slope of the line changes dramatically. In this example, the steep component 202, tail component 204, and differentiation point 206 for the Neutron curve is labeled. Note that the steep component, tail component, and differentiation point for the Gamma curve is different for stilbene, and other compounds which possess good PSD properties. Compounds which do not possess good PSD properties will generally not have substantial differences in the curves plotted for Gamma and Neutron radiation. The upper line in the plot shown in FIG. 2A is a Neutron-induced scintillation pulse shape, while the lower line is a Gamma-induced scintillation pulse shape. As can be seen, stilbene is able to differentiate between the Neutron and Gamma pulse shapes, and produces noticeably different luminescence decay lineshapes for each radiation type. However, not every compound has this ability to separate between Gamma and Neutron pulse shapes, and therefore compounds which do are very useful for PSD, as Gamma and Neutron luminescence decay plots have different pulse shapes for these compounds.

Figure 2B:
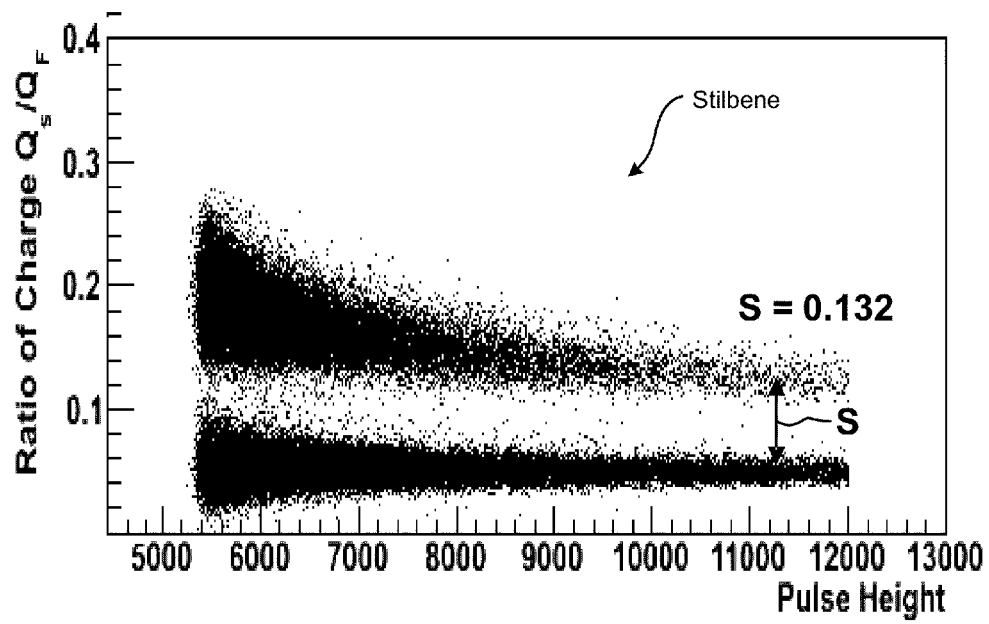
FIG. 2B shows a plot illustrating PSD separation of stilbene according to one embodiment.

Once the population versus time plot has been determined for each test crystal under examination, if it appears that there is PSD for the crystal type, the area ($Q_S$) under the tail component of the curve for each type of radiation is calculated, along with the area ($Q_F$) under the entire line for each type of radiation. By dividing the total area ($Q_F$) into the tail area ($Q_S$), a scatter plot of the ratio of charge versus the pulse height can be produced, as shown in FIG. 2B for stilbene. FIG. 2B shows a plot of the ratio of charge ($Q_S/Q_F$) versus the pulse height, which correlates to an output of a light detector, such as a photomultiplier tube. The x-axis represents the pulse height, which is proportional to the energy of the event. Gamma events correspond to light produced by Compton electrons generated in the detector material. Neutron events correspond to proton recoils in the detector material; lower energy proton recoil events correspond to "glancing angle" interactions between the neutron and proton in the detector material, while a high energy "knock-on" interaction between a neutron and a proton will produce a higher energy event.

Referring to FIG. 2B, at hv equal to about 1600V, stilbene has a neutron-to-gamma (n°/γ) separation S of about 0.132. The greater the separation S of neutron-to-gamma, the better PSD performance can be expected.

It is with these scatter plots that good PSD separation can be determined, which is defined as PSD separation, S, which is the gap between the mean ratio of charge ($Q_S/Q_F$) for Gamma and the mean ratio of charge ($Q_S/Q_F$) for Neutron taken over an extended period of time. The higher this separation, S, is, the better the compound is at PSD separation.

The separation of other materials has been compared to this separation value (0.132) for stilbene, and the results are included below in reference to FIGS. 3-17. Generally, aromatic compounds were tested for fluorescence (indicating efficient scintillation) and for high hydrogen content with low Z constituents (indicating interaction with fast neutrons). Many aspects of each material were studied, including chemical composition, molecular structure, crystallographic structure, crystal size, crystal quality, and crystal impurities.

Figure 3:
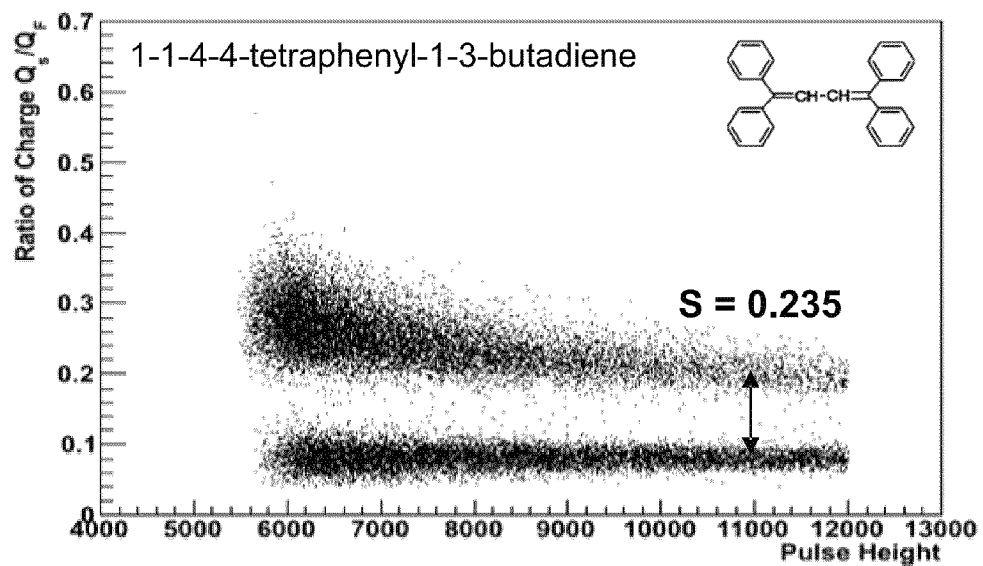
FIG. 3 shows a plot illustrating PSD separation of 1-1-4-4-tetraphenyl-1-3-butadiene according to one embodiment.

In FIG. 3, the PSD separation of 1-1-4-4-tetraphenyl-1-3-butadiene is shown according to some experiments. The measured PSD separation of 0.235 is greater than that of stilbene, which has a PSD separation of about 0.132, and therefore 1-1-4-4-tetraphenyl-1-3-butadiene, in some embodiments, may act as a better scintillator than stilbene.

Figure 4:
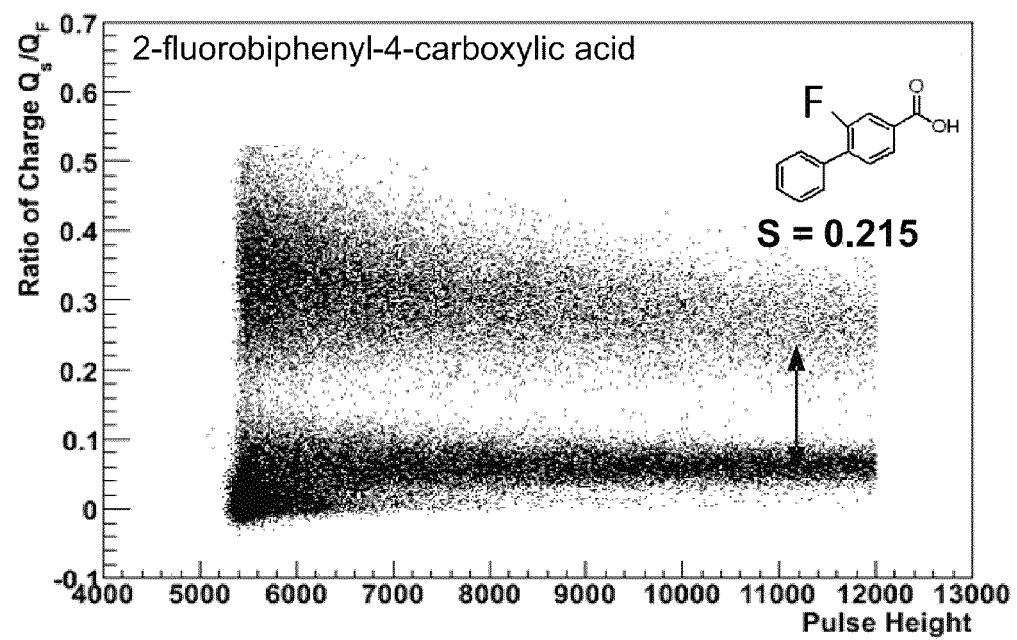
FIG. 4 shows a plot illustrating PSD separation of 2-fluorobiphenyl-4-carboxylic acid according to one embodiment.

In FIG. 4, the PSD separation of 2-fluorobiphenyl-4-carboxylic acid is shown according to some experiments. The measured PSD separation of 0.215 is greater than that of stilbene, which has a PSD separation of about 0.132, and therefore 2-fluorobiphenyl-4-carboxylic acid, in some embodiments, may act as a better scintillator than stilbene.

Figure 5:
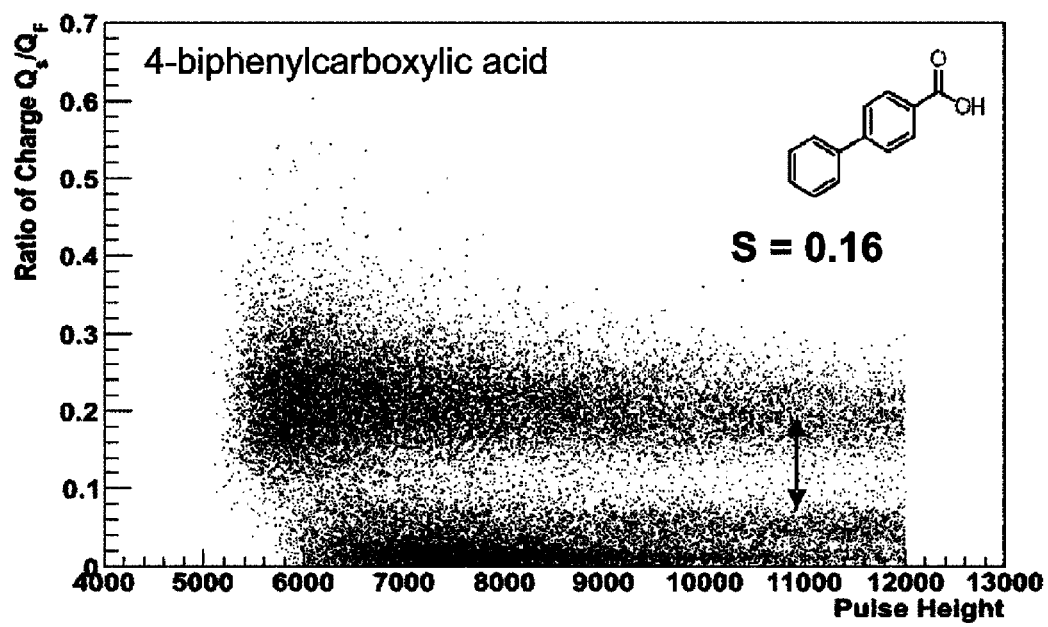
FIG. 5 shows a plot illustrating PSD separation of 4-biphenylcarboxylic acid according to one embodiment.

In FIG. 5, the PSD separation of 4-biphenylcarboxylic acid is shown according to some experiments. The measured PSD separation of 0.16 is greater than that of stilbene, which has a PSD separation of about 0.132, and therefore 4-biphenylcarboxylic acid, in some embodiments, may act as a better scintillator than stilbene.

Figure 6:
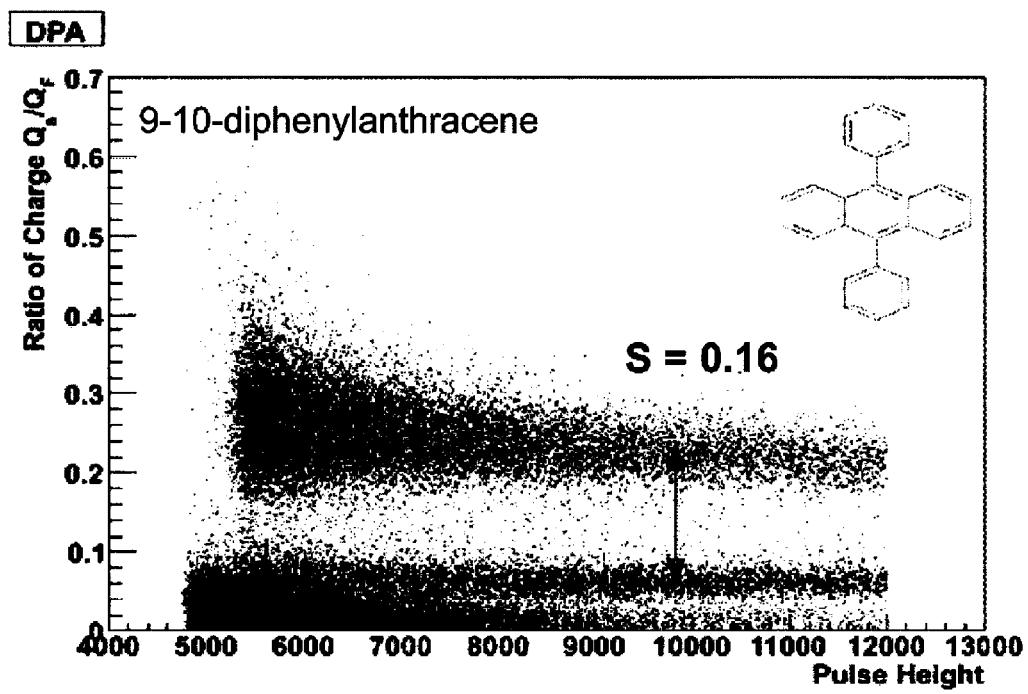
FIG. 6 shows a plot illustrating PSD separation of 9-10-diphenylanthracene according to one embodiment.

In FIG. 6, the PSD separation of 9-10-diphenylanthracene is shown according to some experiments. The measured PSD separation of 0.16 is greater than that of stilbene, which has a PSD separation of about 0.132, and therefore 9-10-diphenylanthracene, in some embodiments, may act as a better scintillator than stilbene.

Figure 7:
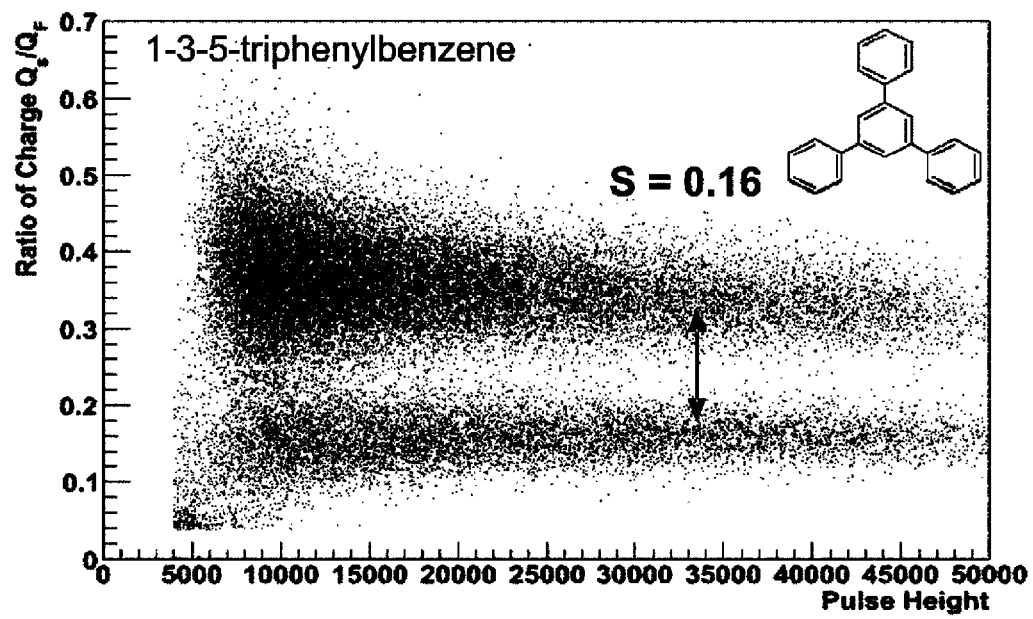
FIG. 7 shows a plot illustrating PSD separation of 1-3-5-triphenylbenzene according to one embodiment.

In FIG. 7, the PSD separation of 1-3-5-triphenylbenzene is shown according to some experiments. The measured PSD separation of 0.16 is greater than that of stilbene, which has a PSD separation of about 0.132, and therefore 1-3-5-triphenylbenzene, in some embodiments, may act as a better scintillator than stilbene.

Figure 8:
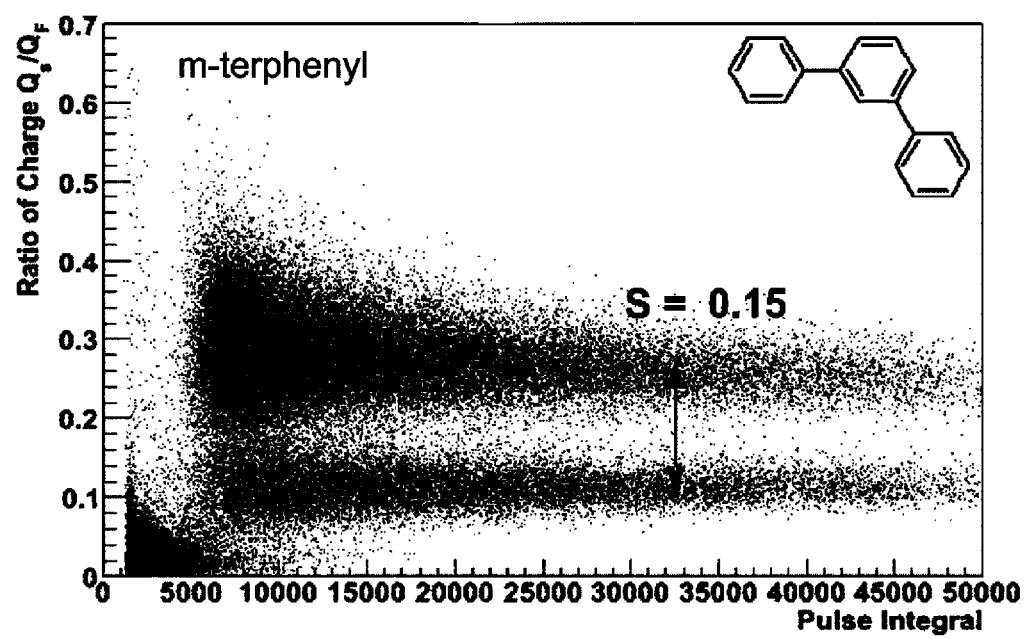
FIG. 8 shows a plot illustrating PSD separation of m-terphenyl according to one embodiment.

In FIG. 8, the PSD separation of m-terphenyl is shown according to some experiments. The measured PSD separation of 0.15 is greater than that of stilbene, which has a PSD separation of about 0.132, and therefore m-terphenyl, in some embodiments, may act as a better scintillator than stilbene.

Figure 9:
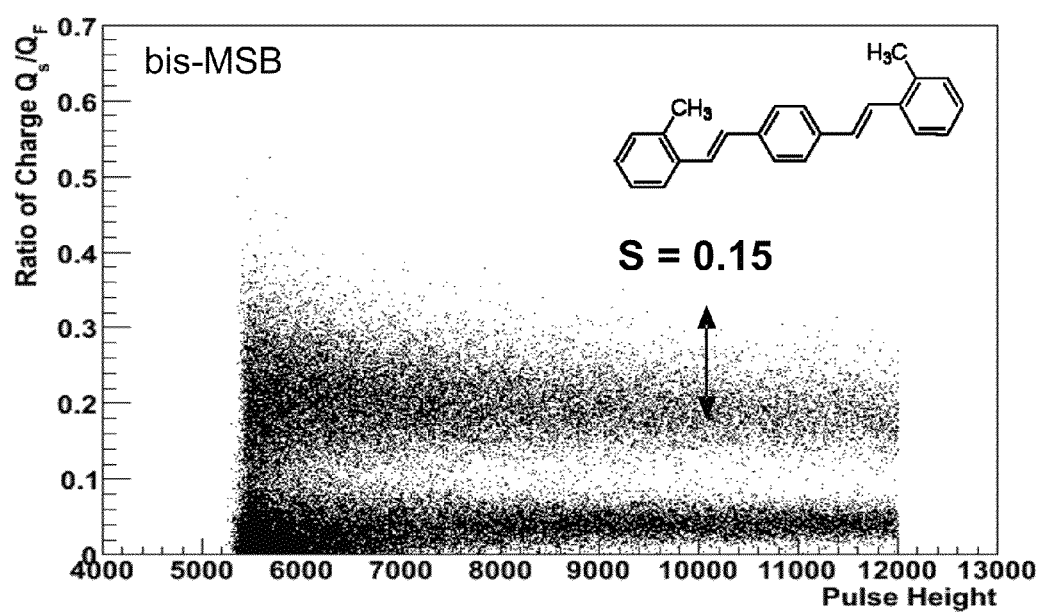
FIG. 9 shows a plot illustrating PSD separation of 1-4-bis (2-methylstyryl)benzene (bis-MSB) according to one embodiment.

In FIG. 9, the PSD separation of 1-4-bis-(2-methylstyryl)-benzene (bis-MSB) is shown according to some experiments. The measured PSD separation of 0.15 is greater than that of stilbene, which has a PSD separation of about 0.132, and therefore bis-MSB, in some embodiments, may act as a better scintillator than stilbene.

Figure 10:
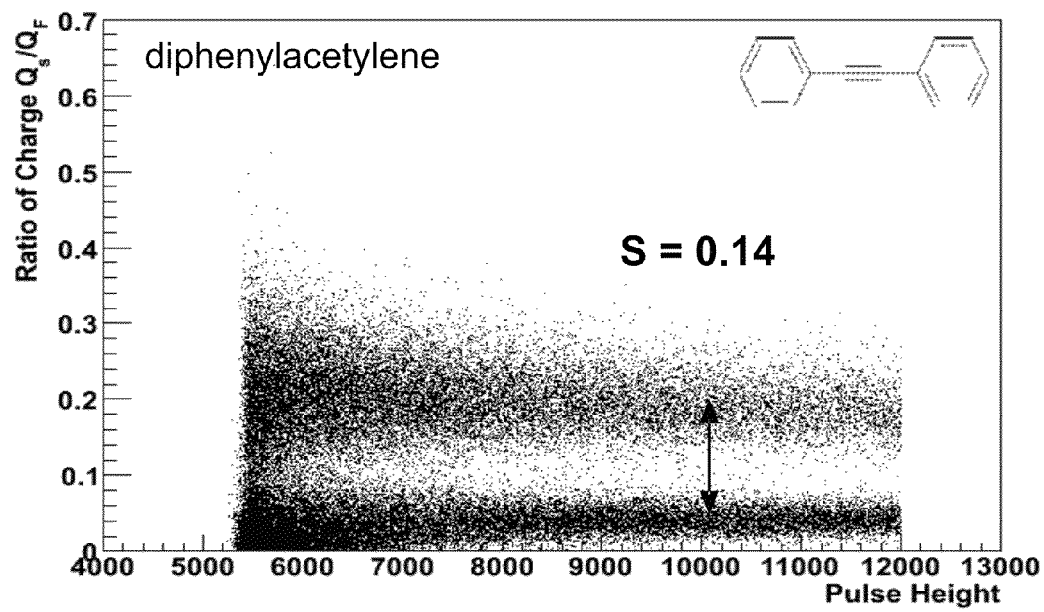
FIG. 10 shows a plot illustrating PSD separation of diphenylacetylene according to one embodiment.

In FIG. 10, the PSD separation of diphenylacetylene is shown according to some experiments. The measured PSD separation of 0.14 is greater than or about the same as that of stilbene, which has a PSD separation of about 0.132, and therefore diphenylacetylene, in some embodiments, may act as good as or even better as a scintillator than stilbene.

Figure 11:
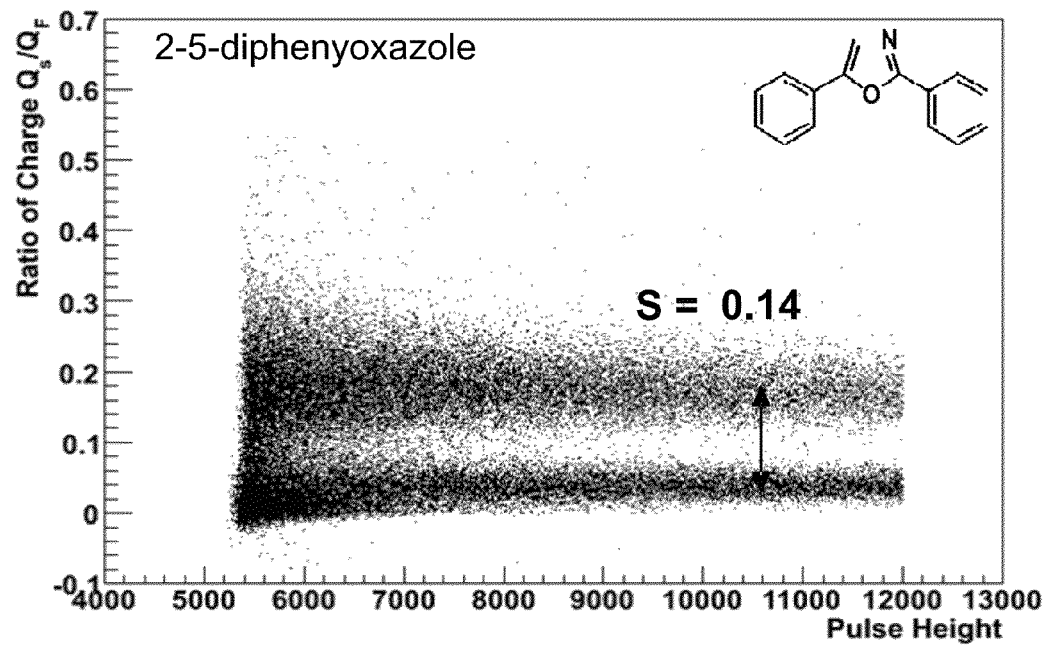
FIG. 11 shows a plot illustrating PSD separation of 2-5-diphenyoxazole according to one embodiment.

In FIG. 11, the PSD separation of 2-5-diphenyoxazole is shown according to some experiments. The measured PSD separation of 0.14 is greater than or about the same as that of stilbene, which has a PSD separation of about 0.132, and therefore 2-5-diphenyoxazole, in some embodiments, may act as good as or even better as a scintillator than stilbene.

Figure 12:
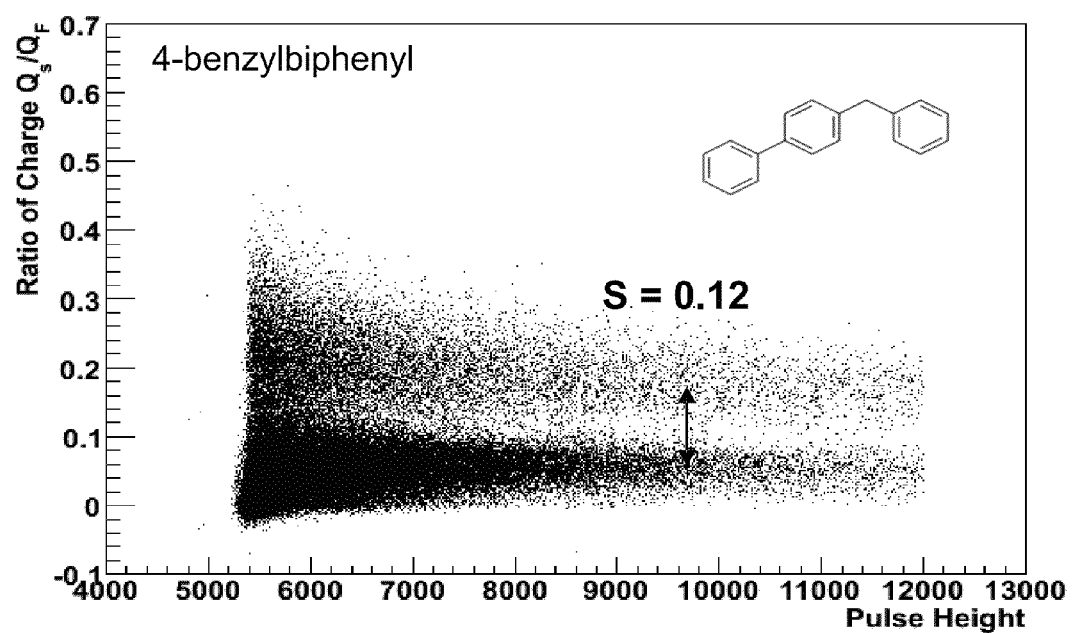
FIG. 12 shows a plot illustrating PSD separation of 4-benzylbiphenyl according to one embodiment.

In FIG. 12, the PSD separation of 4-benzylbiphenyl is shown according to some experiments. The measured PSD separation of 0.12 is a little less than that of stilbene, which has a PSD separation of about 0.132, and therefore 4-benzylbiphenyl, in some embodiments, may act as a good scintillator, possibly comparable to stilbene.

Figure 13:
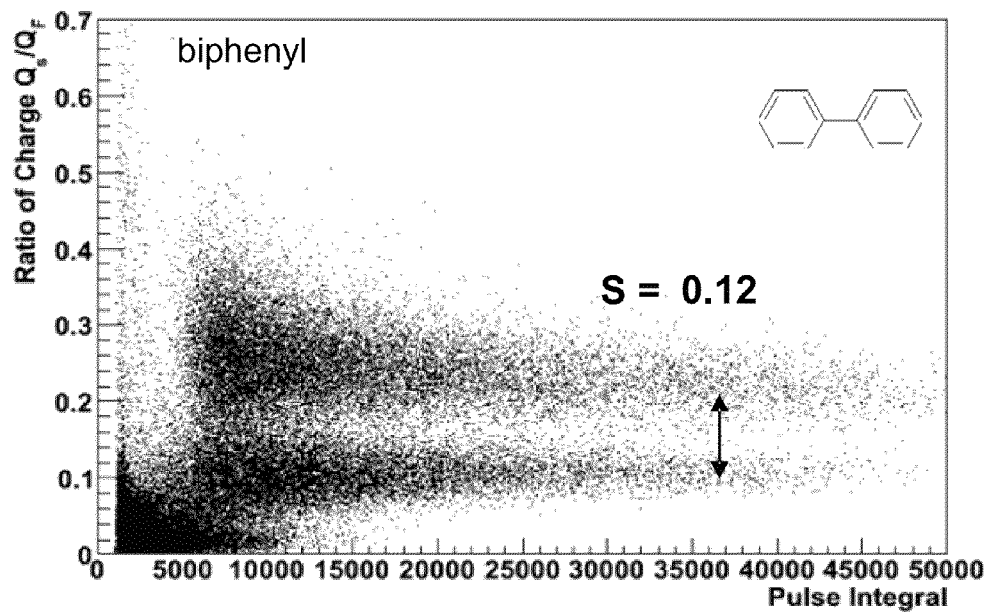
FIG. 13 shows a plot illustrating PSD separation of biphenyl according to one embodiment.

In FIG. 13, the PSD separation of biphenyl is shown according to some experiments. The measured PSD separation of 0.12 is a little less than that of stilbene, which has a PSD separation of about 0.132, and therefore biphenyl, in some embodiments, may act as a good scintillator, possibly comparable to stilbene.

Figure 14:
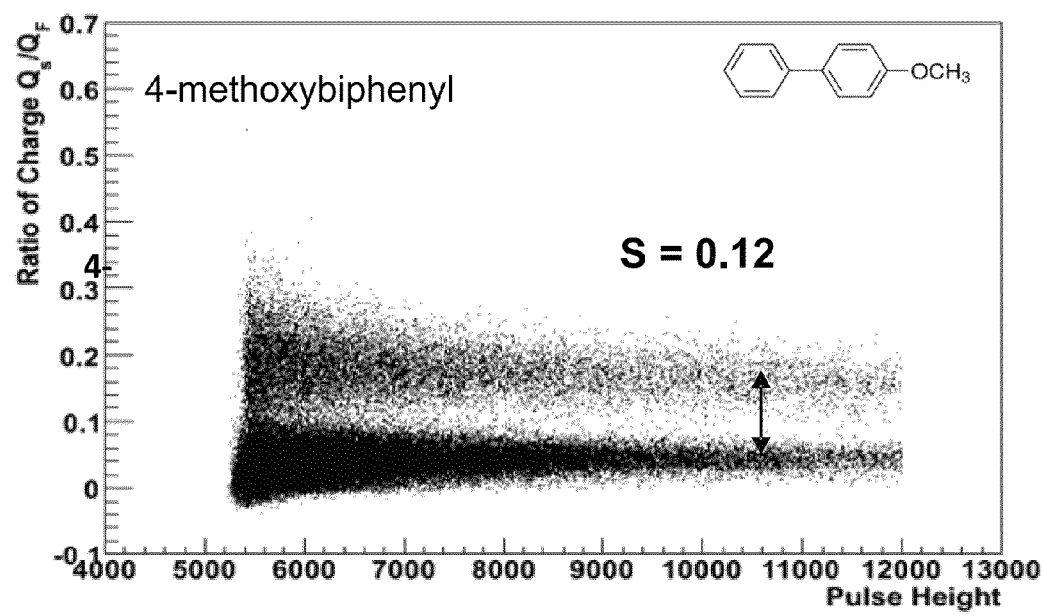
FIG. 14 shows a plot illustrating PSD separation of 4-methoxybiphenyl according to one embodiment.

In FIG. 14, the PSD separation of 4-methoxybiphenyl is shown according to some experiments. The measured PSD separation of 0.12 is a little less than that of stilbene, which has a PSD separation of about 0.132, and therefore 4-methoxybiphenyl, in some embodiments, may act as a good scintillator, possibly comparable to stilbene.

Figure 15:
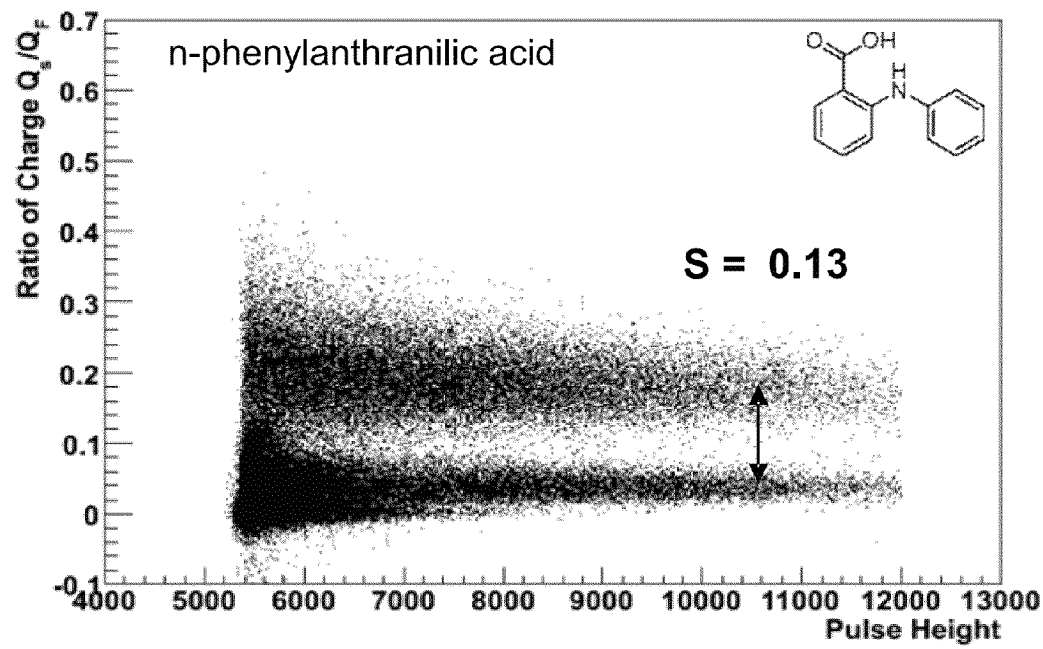
FIG. 15 shows a plot illustrating PSD separation of n-phenylanthranilic acid according to one embodiment.

In FIG. 15, the PSD separation of n-phenylanthranilic acid is shown according to some experiments. The measured PSD separation of 0.13 is a little less than that of stilbene, which has a PSD separation of about 0.132, and therefore n-phenylanthranilic acid, in some embodiments, may act as a good scintillator, possibly comparable to stilbene.

Figure 16:
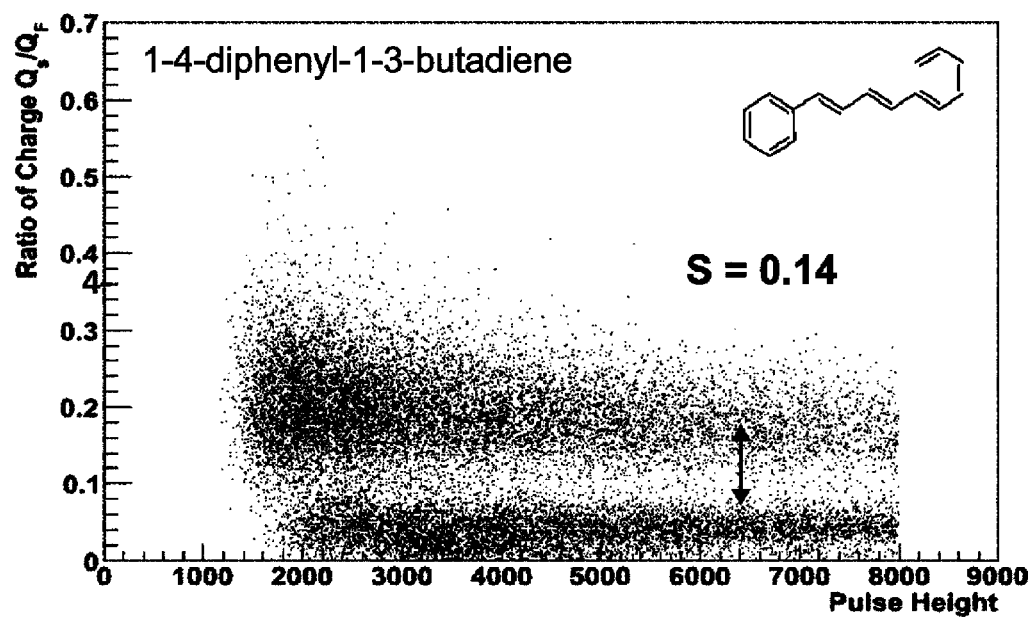
FIG. 16 shows a plot illustrating PSD separation of 1-4-diphenyl-1-3-butadiene according to one embodiment.

In FIG. 16, the PSD separation of 1-4-diphenyl-1-3-butadiene is shown according to some experiments. The measured PSD separation of 0.14 is greater than or about the same as that of stilbene, which has a PSD separation of about 0.132, and therefore 1-4-diphenyl-1-3-butadiene, in some embodiments, may act as good as or even better as a scintillator than stilbene.

Figure 17:
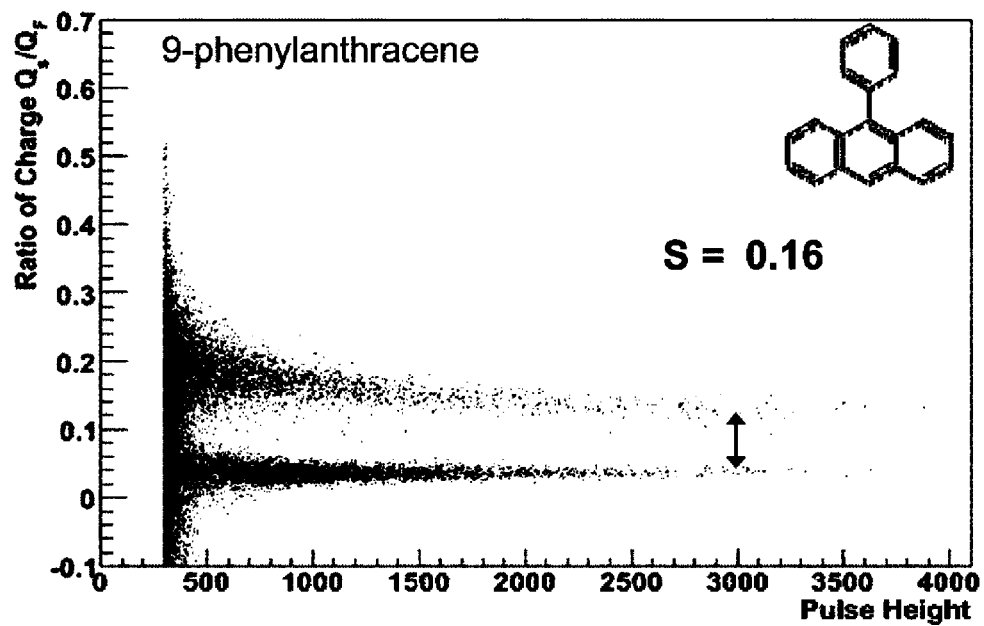
FIG. 17 shows a plot illustrating PSD separation of 9-phenylanthracene according to one embodiment.

In FIG. 17, the PSD separation of 9-phenylanthracene is shown according to some experiments. The measured PSD separation of 0.16 is greater than that of stilbene, which has a PSD separation of about 0.132, and therefore 9-phenylanthracene, in some embodiments, may act as a better scintillator than stilbene.

Of course, many crystals tested did not perform as well as stilbene. Some of these crystal compounds include 4-4'-dimethyltransstilbene, 3-phenylsalicylic acid, 2-methoxybenzoic acid, dibenzofuran, and 2-naphthoic acid with a PSD separation of 0.09, methyl-4-phenylbenzoate and 2-3-bis(4-bromophenyl)quinoxaline (BBQ) with a PSD separation of 0.08, triphenylmethane, triphenylmethanol, phenanthrene, and carbazole with a PSD separation of 0.07, salicylamide, 4-methoxysalicyclic acid, and o-toluic acid with a PSD separation of 0.06, ammonium salicylate and lithium salicylate with a PSD separation of 0.04. These compounds may be useful as scintillators, but with these lower PSD separation properties, they may be limited in their ability to distinguish between neutron and gamma radiation types. Other crystal compounds which were tested but did not display any significant PSD separation include but are not limited to the following selected compounds: bibenzyl, tetraphenylethylene, triphenylene, and fluorene. Many other crystal compounds were tested and did not display any significant PSD separation properties, but are excluded here for the sake of brevity.

According to some embodiments, a substantially pure crystal exhibiting an optical response signature for neutrons that is different than an optical response signature for gamma rays (i.e., having good PSD properties) comprises a material selected from a group consisting of: 1-1-4-4-tetraphenyl-1-3-butadiene, 2-fluorobiphenyl-4-carboxylic acid, 4-biphenylcarboxylic acid, 9-10-diphenylanthracene, 9-phenylanthracene, 1-3-5-triphenylbenzene, m-terphenyl, bis-MSB, diphenylacetylene, 2-5-diphenyoxazole, 4-benzylbiphenyl, biphenyl, 4-methoxybiphenyl, n-phenylanthranilic acid, and 1-4-diphenyl-1-3-butadiene. In addition, the signature may be different for each type of material and/or neutron source, but a given material will tend to show similar response for a given neutron type and/or source.

In some approaches, the substantially pure crystal may be grown exclusively from solution or may be formed by melt growth. Other methods of forming the substantially pure crystal may be used also.

In more approaches, the substantially pure crystal may be a chemical derivative and/or isomers of the material.

In some embodiments, the substantially pure crystal may have physical characteristics of formation from solution including faceted growth on at least one face of the substantially pure crystal.

Also, the substantially pure crystal may have a length of greater than 1 mm in one dimension, according to some embodiments. In further embodiments, the substantially pure crystal may have a length of greater than 5 mm in one dimension. Larger and smaller sizes than the foregoing ranges are also contemplated, e.g., less than 1 mm, greater than about 25 mm, etc.

Figure 18:
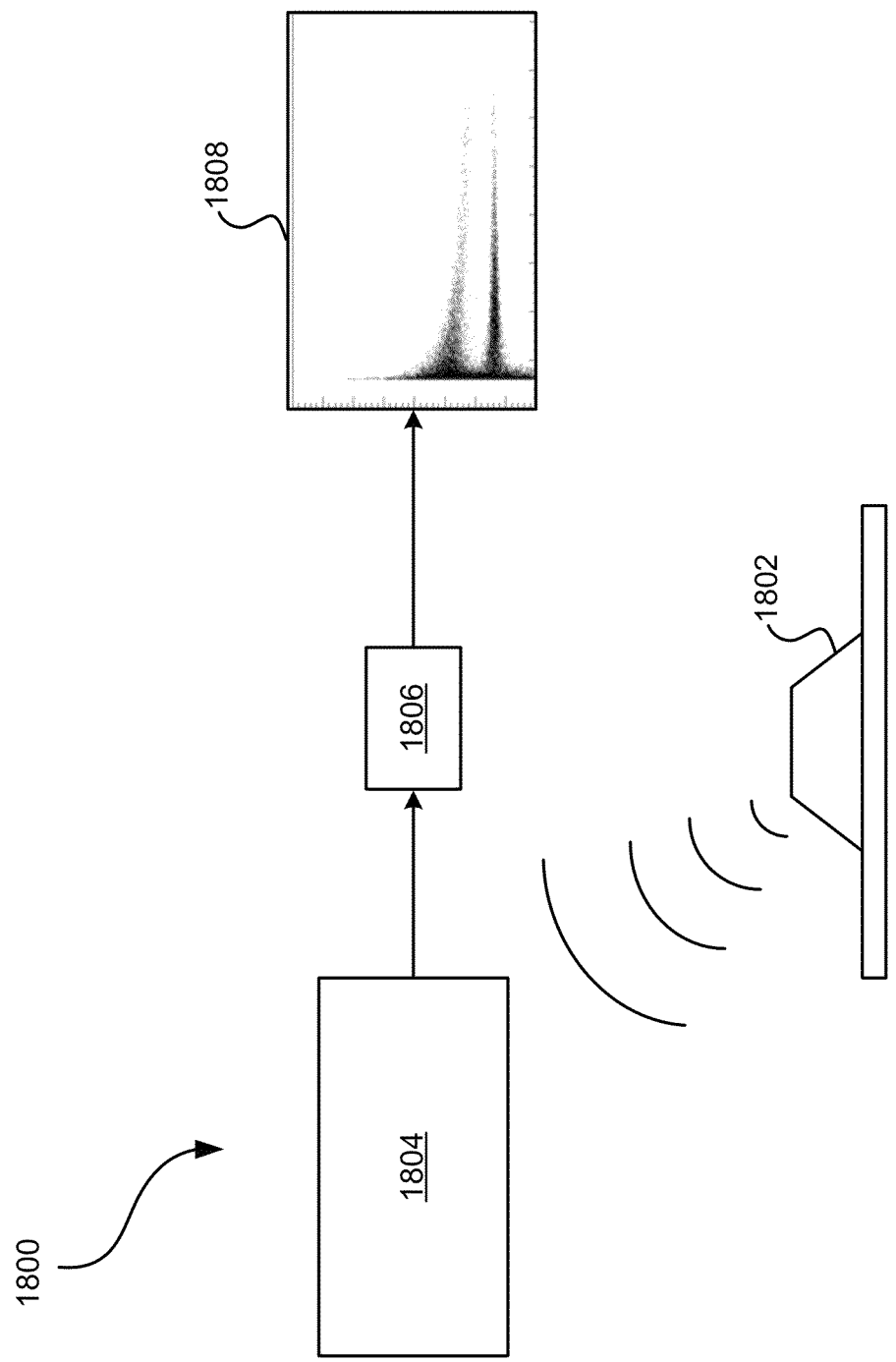
FIG. 18 shows a simplified schematic layout of a system that may use crystals described herein.

A simplified schematic layout of a system is shown in FIG. 18 according to one embodiment. The system 1800 comprises a substantially pure crystal 1802, such as one of those described herein. The system 1800 also includes a photodetector 1804, such as a photomultiplier tube, which can detect light emitted from the material 1802, and detect the response of the material to at least one of neutron and gamma ray irradiation.

In some embodiments, the system 1800 may further comprise a processor 1806 for performing a discrimination method for processing an output of the photodetector 1804 using pulse shape discrimination for differentiating responses of the material 1802 to the neutron and gamma ray irradiation. The result of the discrimination method may be displayed on a display device 1808 in any form, such as in a plot of the PSD separation, similar to those plots shown in FIGS. 3-17.

According to one embodiment, a material exhibiting an optical response signature for neutrons that is different than an optical response signature for gamma rays exhibits performance comparable to or superior to stilbene in terms of distinguishing neutrons from gamma rays, and the material is not stilbene.

In some approaches, the material is in the form of a crystal, wherein the crystal has physical characteristics of formation from solution including faceted growth on at least one face of the crystal. In further approaches, the crystal has a length of greater than 1 mm in one dimension. In more approaches, the crystal may have a length of greater than 5 mm in one dimension. Larger and smaller sizes than the foregoing ranges are also contemplated, e.g., less than 1 mm, greater than about 25 mm, etc.

According to some embodiments, the material may include a molecule having two or more phenyl groups and continuous conjugation throughout the molecule.

Additionally, in some embodiments, the material may be selected from a group consisting of: 1-1-4-4-tetraphenyl-1-3-butadiene, 2-fluorobiphenyl-4-carboxylic acid, 4-biphenylcarboxylic acid, 9-10-diphenylanthracene, 9-phenylanthracene, 1-3-5-triphenylbenzene, m-terphenyl, bis-MSB, diphenylacetylene, 2-5-diphenyoxazole, 4-benzylbiphenyl, biphenyl, 4-methoxybiphenyl, n-phenylanthranilic acid, and 1-4-diphenyl-1-3-butadiene.

According to some embodiments of the invention, many beneficial uses may be derived. For example, some embodiments may be useful for detection of illicit nuclear weapons at ports of entry, at security checkpoints, at sensitive city installations, in scanning equipment for wide area sweeping, at off shore facilities, on ships and/or boats, etc. Some embodiments may be useful for monitoring of nuclear power plants for dangerous and/or unhealthy levels of radiation, for leakage detection, etc. Also, some embodiments may be used for the measurement of neutrons emanating from special nuclear material, possibly by further using coincidence detection (registering the nuclear multiplicity) and/or on the basis of active interrogation methods. Also, some embodiments may be used for scientific measurements of neutron emitters, such as in diverse high energy physics experiments and neutron imaging applications.

The novel systems disclosed herein may be formed by any method, including melt growth, solution growth, natural crystal discovery, etc. Various growth techniques known in the art may be used. Illustrative methods for forming organic crystals from solution, including at least some of those materials herein, are described in U.S. Pat. No. 8,207,507 to Zaitseva et al., having title "Solution-Grown Crystals for Neutron Radiation Detectors, and Methods of Solution Growth," which is herein incorporated by reference.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A material exhibiting an optical response signature for neutrons that is different than an optical response signature for gamma rays, said material exhibiting performance comparable to or superior to stilbene in terms of distinguishing neutrons from gamma rays, wherein the material is not stilbene, the material comprising a molecular motif selected from a group consisting of:
   two or more benzene rings,
   one or more benzene rings with a carboxylic acid group,
   one or more benzene rings with at least one double bond adjacent to at least one of the one or more benzene rings, and
   one or more six-member rings comprising:
      carbon atoms; and
      at least one non-carbon atom,
      wherein each atom in each six-member ring is double-bonded to one other atom in the six-member ring, and
   wherein the material is in the form of a crystal having physical characteristics of formation from solution, the physical characteristics including faceted growth on at least one face of the crystal.

2. The material of claim 1, wherein at least about 95 mol % of the crystal is the material.

3. The material of claim 1, wherein the crystal has a length of greater than 1 mm in one dimension.

4. The material of claim 1, wherein the material is in the form of a crystal, wherein the crystal has a length of less than 1 mm in one dimension.

5. The material of claim 1, wherein the crystal has a length of greater than 5 mm in one dimension.

6. The material of claim 1, wherein the material includes a molecule having two or more phenyl groups and continuous conjugation throughout the molecule.

7. The material of claim 1, wherein the material is selected from a group consisting of:
   1-1-4-4-tetraphenyl-1-3-butadiene;
   2-fluorobiphenyl-4-carboxylic acid;
   4-biphenylcarboxylic acid;
   9-10-diphenylanthracene;
   9-phenyl anthracene;
   1-3-5-triphenylbenzene;
   m-terphenyl;
   bis-MSB;
   diphenylacetylene;
   2-5-diphenyoxazole;
   4-benzylbiphenyl;
   biphenyl;
   4-methoxybiphenyl;
   n-phenylanthranilic acid; and
   1-4-diphenyl-1-3-butadiene.

8. The material of claim 1, the physical characteristics including faceted growth on at least two faces of the crystal.

9. A system, comprising:
   the material of claim 1; and
   a photodetector for detecting the response of the material to neutron and gamma ray irradiation.

10. The system of claim 9, further comprising a processor for performing a discrimination method for processing an output of the photodetector using pulse shape discrimination for differentiating responses of the material to the neutron and gamma ray irradiation.

11. The system of claim 10, further comprising a display device for outputting a result of the processing.

12. A method, comprising:
   growing an organic crystal from solution, the organic crystal exhibiting an optical response signature for neutrons that is different than an optical response signature for gamma rays, said organic crystal exhibiting performance comparable to or superior to stilbene in terms of distinguishing neutrons from gamma rays, wherein the material is not stilbene.

13. The method of claim 12, wherein the crystal comprises a material selected from a group consisting of:
   1-1-4-4-tetraphenyl-1-3-butadiene;
   2-fluorobiphenyl-4-carboxylic acid;
   4-biphenylcarboxylic acid;
   9-10-diphenylanthracene;
   9-phenylanthracene;
   1-3-5-triphenylbenzene;
   m-terphenyl;
   bis-MSB;
   diphenylacetylene;
   2-5-diphenyoxazole;
   4-benzylbiphenyl;
   biphenyl;
   4-methoxybiphenyl;
   n-phenylanthranilic acid; and
   1-4-diphenyl-1-3-butadiene.

14. The method of claim 12, the crystal comprising a molecular motif selected from a group consisting of:
   two or more benzene rings,
   one or more benzene rings with a carboxylic acid group,
   one or more benzene rings with at least one double bond adjacent to at least one of the one or more benzene rings, and
   one or more six-member rings comprising:
      carbon atoms; and at least one non-carbon atom,
wherein each atom in each six-member ring is double-bonded to one other atom in the six-member ring.

15. The method of claim 12, wherein the crystal has a length of greater than 1 mm in one dimension.

16. The method of claim 12, wherein the crystal has a length of greater than 5 mm in one dimension.

17. The method of claim 12, wherein the crystal has a length of greater than 25 mm in one dimension.

18. The method of claim 12, said solution being comprised of a solvent and a solute, said solvent comprising more than 30% of said solution, and said solution being held at a temperature that is less than that of the melting point of said solute during the growing.

* * * * *